US009056086B2

(12) United States Patent
Manku et al.

(10) Patent No.: US 9,056,086 B2
(45) Date of Patent: *Jun. 16, 2015

(54) PHARMACEUTICAL COMPOSITIONS COMPRISING DGLA, 15-HEPE, AND/OR 15-HETRE AND METHODS OF USE THEREOF

(71) Applicant: Dignity Sciences Limited, Dublin (IE)

(72) Inventors: Mehar Manku, Birmingham (GB); John Climax, Dublin (IE); David Coughlan, Dublin (IE)

(73) Assignee: Dignity Sciences Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,120

(22) Filed: Sep. 18, 2012

(65) Prior Publication Data

US 2013/0102575 A1 Apr. 25, 2013

Related U.S. Application Data

(63) Continuation of application No. 13/478,982, filed on May 23, 2012, now Pat. No. 8,293,790.

(60) Provisional application No. 61/549,018, filed on Oct. 19, 2011.

(51) Int. Cl.
| | |
|---|---|
| *A61K 31/19* | (2006.01) |
| *A61K 31/202* | (2006.01) |
| *A61K 31/192* | (2006.01) |
| *A61K 31/327* | (2006.01) |
| *A61K 45/06* | (2006.01) |
| *A61K 9/00* | (2006.01) |
| *A61K 8/36* | (2006.01) |
| *A61K 8/368* | (2006.01) |
| *A61K 8/38* | (2006.01) |
| *A61K 8/49* | (2006.01) |
| *A61K 8/67* | (2006.01) |
| *A61Q 19/00* | (2006.01) |

(52) U.S. Cl.
CPC ............... *A61K 31/202* (2013.01); *A61K 31/19* (2013.01); *A61K 31/192* (2013.01); *A61K 31/327* (2013.01); *A61K 45/06* (2013.01); *A61K 9/0014* (2013.01); *A61K 8/361* (2013.01); *A61K 8/368* (2013.01); *A61K 8/38* (2013.01); *A61K 8/4946* (2013.01); *A61K 8/675* (2013.01); *A61Q 19/00* (2013.01)

(58) Field of Classification Search
CPC ...................................................... A61K 31/19
USPC ........................................................ 514/560
See application file for complete search history.

(56) References Cited

U.S. PATENT DOCUMENTS

| | | | |
|---|---|---|---|
| 4,273,763 A | 6/1981 | Horrobin | |
| 4,309,415 A | 1/1982 | Horrobin | |
| 4,386,072 A | 5/1983 | Horrobin et al. | |
| 4,388,324 A | 6/1983 | Horrobin | |
| 4,444,755 A * | 4/1984 | Horrobin | ...................... 424/642 |
| 4,826,877 A | 5/1989 | Stewart et al. | |
| 4,888,326 A | 12/1989 | Horrobin | |
| 4,898,885 A | 2/1990 | Horrobin | |
| 4,965,075 A | 10/1990 | Horrobin et al. | |
| 4,970,076 A | 11/1990 | Horrobin | |
| 4,996,233 A | 2/1991 | Horrobin | |
| 4,997,657 A | 3/1991 | Horrobin et al. | |
| 5,145,686 A | 9/1992 | Horrobin et al. | |
| 5,198,468 A | 3/1993 | Horrobin | |
| 5,312,834 A | 5/1994 | Yeo | |
| 5,318,991 A | 6/1994 | Horrobin et al. | |
| 5,324,748 A | 6/1994 | Horrobin | |
| 5,328,691 A | 7/1994 | Horrobin et al. | |
| 5,380,757 A | 1/1995 | Horrobin | |
| 5,409,955 A | 4/1995 | Bockow et al. | |
| 5,552,150 A | 9/1996 | Horrobin et al. | |
| 5,562,913 A | 10/1996 | Horrobin | |
| 5,580,556 A | 12/1996 | Horrobin | |
| 5,583,159 A | 12/1996 | Horrobin et al. | |
| 5,589,509 A | 12/1996 | Horrobin | |
| 5,614,208 A | 3/1997 | Horrobin et al. | |
| 5,618,558 A | 4/1997 | Horrobin et al. | |
| 5,620,701 A | 4/1997 | Horrobin et al. | |
| 5,663,202 A | 9/1997 | Horrobin et al. | |
| 5,709,855 A | 1/1998 | Bockow et al. | |
| 5,888,541 A | 3/1999 | Horrobin et al. | |
| 6,069,168 A | 5/2000 | Horrobin et al. | |

(Continued)

FOREIGN PATENT DOCUMENTS

| | | |
|---|---|---|
| CN | 1104496 A | 7/1995 |
| EP | 0139480 | 5/1952 |

(Continued)

OTHER PUBLICATIONS

Chen, Yung-Chih et al.; "Therapeutic Effect of Topical Gamma-Linolenic Acid on Refractory Uremic Pruritus"; American Journal of Kidney Diseases, vol. 48, No. 1, Jul. 2006, pp. 69-76.
Conrow et al., Org. Proc. Res. & Dev. 15:301-304 (2011).
Desbois et al., "Antibacterial free fatty acids: activities, mechanisms of action and biotechnological potential," Appl. Microbiol. Biotechnol., (2010) 85:1629-1642.
Dewsbury, E. et al.; "Topical eicosapentaenoic acid (EPA) in the treatment of psoriasis" British Journal of Dematology (1989) 120, pp. 518-584.
Elshof et al. "Biocatalytic large-scale production of 12(S)-hydroperoxy-9(Z), 11∈octadecadienoic acid from hydrolysed safflower oil by a crude soybean-flour extract as lipoxygenase source," Rec. Tray. Chim Pays-Bas, 115, 11-12, p. 499-504 (1996).

(Continued)

*Primary Examiner* — Raymond Henley, III
(74) *Attorney, Agent, or Firm* — Perkins Coie LLP

(57) ABSTRACT

The present disclosure provides compositions comprising fatty acids, or derivatives thereof (e.g., C1-C4 esters) including, for example, DGLA, 15-OHEPA and/or 15-HETrE, used singly or in combination with anti-bacterial agents for the treatment of disease and/or disorders such as acne or atopic dermatitis.

44 Claims, No Drawings

(56) References Cited

U.S. PATENT DOCUMENTS

| | | | |
|---|---|---|---|
| 6,177,470 | B1 | 1/2001 | Horrobin et al. |
| 6,479,544 | B1 | 11/2002 | Horrobin |
| 6,630,157 | B1 | 10/2003 | Horrobin et al. |
| 8,293,790 | B2 * | 10/2012 | Manku et al. ............ 514/549 |
| 2002/0198177 | A1 | 12/2002 | Horrobin |
| 2003/0073930 | A1 | 4/2003 | Morrissey et al. |
| 2003/0194446 | A1 | 10/2003 | Akes et al. |
| 2006/0009522 | A1 | 1/2006 | Dana et al. |
| 2006/0257352 | A1 | 11/2006 | Saar |
| 2007/0015438 | A1 | 1/2007 | Lange et al. |
| 2007/0105954 | A1 | 5/2007 | Puri |
| 2008/0125487 | A1 | 5/2008 | Das et al. |
| 2008/0161275 | A1 | 7/2008 | Gjorstrup |
| 2008/0213357 | A1 | 9/2008 | Hebard et al. |
| 2009/0176284 | A1 | 7/2009 | Furihata et al. |
| 2010/0184727 | A1 | 7/2010 | Roach et al. |
| 2010/0278948 | A1 | 11/2010 | Courtin |
| 2010/0317735 | A1 | 12/2010 | Hong et al. |
| 2011/0015415 | A1 | 1/2011 | Singh et al. |
| 2011/0016585 | A1 | 1/2011 | Pereira et al. |
| 2011/0039010 | A1 | 2/2011 | Rein et al. |
| 2011/0059885 | A1 | 3/2011 | Lea et al. |
| 2011/0082216 | A1 | 4/2011 | Wu et al. |
| 2012/0142773 | A1 | 6/2012 | Kelliher et al. |
| 2012/0213824 | A1 | 8/2012 | Kelliher et al. |
| 2012/0232147 | A1 | 9/2012 | Manku et al. |
| 2012/0264705 | A1 | 10/2012 | Manku et al. |
| 2013/0101533 | A1 | 4/2013 | Manku et al. |
| 2013/0102575 | A1 | 4/2013 | Manku et al. |
| 2013/0267598 | A1 | 10/2013 | Manku et al. |
| 2013/0274338 | A1 | 10/2013 | Manku et al. |
| 2013/0331448 | A1 | 12/2013 | Manku et al. |

FOREIGN PATENT DOCUMENTS

| | | |
|---|---|---|
| EP | 0035856 | 9/1981 |
| EP | 0037175 | 10/1981 |
| EP | 0078434 | 5/1983 |
| EP | 0087863 | 9/1983 |
| EP | 0087864 | 9/1983 |
| EP | 0087865 | 9/1983 |
| EP | 0115419 | 8/1984 |
| EP | 0132089 | 1/1985 |
| EP | 0173478 | 3/1986 |
| EP | 0309086 | 3/1989 |
| EP | 0409559 | 1/1991 |
| EP | 0416855 | 3/1991 |
| EP | 1852114 | 11/2007 |
| EP | 2118126 A1 | 11/2009 |
| EP | 2508180 | 10/2012 |
| JP | A-S52-64452 | 5/1977 |
| JP | A-S52-66659 | 6/1977 |
| JP | 4-290820 | 10/1992 |
| JP | 2006219454 | 8/2006 |
| JP | 2006306812 | 11/2006 |
| WO | WO9014824 | 12/1990 |
| WO | WO9816215 | 4/1998 |
| WO | WO9852556 | 11/1998 |
| WO | WO00/20603 | 4/2000 |
| WO | WO0103696 | 1/2001 |
| WO | WO0201969 | 1/2002 |
| WO | WO02089791 | 11/2002 |
| WO | WO02092071 | 11/2002 |
| WO | WO02096408 | 12/2002 |
| WO | WO2007079224 | 7/2007 |
| WO | WO2008070129 | 6/2008 |
| WO | WO2008114141 | 9/2008 |
| WO | WO2010125330 | 11/2010 |
| WO | WO2010125340 | 11/2010 |
| WO | WO2012087745 | 6/2012 |
| WO | WO2013057284 | 4/2013 |
| WO | WO2013057287 | 4/2013 |
| WO | WO2013082265 | 6/2013 |
| WO | WO2013112876 | 8/2013 |
| WO | WO2013124479 | 8/2013 |
| WO | WO2014022816 | 2/2014 |
| WO | WO2014118097 | 8/2014 |

OTHER PUBLICATIONS

Elshof et al., "Biocatalytic hydroxylation of linoleic acid in a double-fed batch system with lipoxygenase and cysteine," 100:6, pp. 246-251 (1999).

Erythema, Retrieved online [Feb. 11, 2014], Retrieved from URL:<http://umm.edu/health/medical/altmed/condition/erythema>.

Feldlaufer et al., "Antimicrobial activity of fatty acids aganst Bacillus larvae, the causative agent of American Foulbrood disease," Apidologie (1993) 24. pp. 95-99.

Horrobin D. F.; "Nutritional and Medical Importance of Gamma-Linolenic Acid"; Prog. lipid Res. vol. 31, No. 2. pp. 163-194, 1992.

Huang et al., "Antimicrobial activity of n-6, n-7 and n-9 fatty acids and their esters for oral microorganisms," Archives of Oral Biology, 55 (2010), pp. 555-560.

Kanehara, S. et al.; "Undershirts coated with borage oil alleviate the symptoms of atopic dermatitis in children" ; EJD, vol. 17, No. 5, Sep.-Oct. 2007, 2 pages.

Kawashima et al., "Subchronic (13-week) oral toxicity study of dihomo-y-linolenic acid (DGLA) oil in rats," Food and Chemical Toxicology (2009).

Kiistala et al., "In vivo Separation of Epidermis by Production of Suction Blister," Lancet 1964:1444-1445 (1964).

Kiistala, "Suction blister device for separation fo viable epidermis from dermis," J. Invest. Dermatol. 50:129-137 (1968).

Kawamura, A. et al.; "Dietary Supplemental of Gamma-Linolenic Acid Improves Skin Parameters in Subjects with Dry Skin and Atopic Dermatitis"; Journal of oleo Science; vol. 60, No. 12, pp. 597-607, 2011.

Miller, C. C. et al.; Induction of Epidermal Hyperproliferation by Topical n-3 Ployunsaturated Fatty Acids on Guinea Pig Skin Linked to Decreased Levels of 13-Hydroxyoctadecadienoic Acid (13-Hode); The Journal of Investigative Dermatology, vol. 94, No. 3, Mar. 1990, 7 pages.

Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. Of Invest. Dermatol., vol. 96, No. 1, pp. 98-103 (1991).

Miller et al., "Guinea Pig Epidermins Generates Putative Anti-Inflammatory Metabolites from Fish Oil Polyunsaturated Acids," Lipids, vol. 24, No. 12 (1989).

Mosmann, "Rapid Colorimetric Assay for Cellular Growth and Survival: Application to Proliferation and Cytotoxicity Assays," J. Immunol. Meth. vol. 65, pp. 55-63 (1983).

Mundlein et al., "Comparison of Transepiderminal Water Losee (TEWL) Measurements with Two Novel Sensors Based on Different Sensing Principles," Sensors and Actuators A: Physical, 142(1):67-72 (2008).

Nijs et al., "Adult-onset asthma, is it really different?" Eur. Respir. Rev., vol. 22(127), pp. 44-52, Mar. 1, 2013.

PCT/EP12/070809 International Search Report dated Jan. 22, 2013.

PCT/EP12/070813 International Search Report dated Jan. 14, 2013.

PCT/EP2013/053677 International Search Report dated Jun. 19, 2013.

PCT/GB2010/000844 International Search Report dated Jul. 19, 2010.

PCT/US2012/67030 International Search Report dated Feb. 5, 2013.

PCT/US2013/023201 International Search Report dated Mar. 29, 2013.

PCT/US2013/053498 International Search Report dated Feb. 4, 2014.

Salgo et al., "Microdialysis documents changes in the micromilieu of psoriatic plaques under continuous systemic therapy," Experimental Dermatology 20:130-133 (2011).

Schreiner et al., "Transfer of Penicillin G and Ampicillin into Human Skin Blisters Induced by Suction," Scand. Journ. Infect. Dis. 14(Suppl.):233-237 (1978).

(56) References Cited

OTHER PUBLICATIONS

Schwartz et al., "Antifungal properties of polymyxin B and its potentiation of tetracycline as an antifungal agent," Antimicrobial Chemother. 1972 Jul, 2(1):36-40.
Stillman, M. A. et al.; "Relative irritancy of free fatty acids of different chain length"; Contact Dermatitis, 1975, 1, pp. 65-69.
Suda et al., Agric. Food Chem. 43, 3, 1995, p. 742.
Thiboutot, et al.; New insights into the management of acne: an update from Global Alliance to Improve Outcomes in Acne Group; J Am Acad Dermatol, May 2009, vol. 60, No. 5, 50 pages.
Tope, "Multi-electrode radio frequency resurfacing of ex vivo homan skin," Dermatol. Surg., 25:348-52 (1999).
Uchida, A. et al.; "Antibacterial and Antialgal Substances Produced by the Dinoflagellate Peridinium bipes"; Nippon Sisan Gakkaishi : Formerly Bull. japan. Soc. Sci. Fish., vol. 54, No. 11, (1998), pp. 1941-1945.
Watanabe, T. et al.; "The effect of a newly developed ointment containing eicosapentaenoic acid and docosahexaenoic acid in the treatment of atopic dermatitis" ; The Journal of Medicine Investigation; vol. 46, 1999, 5 pages.
Wilgus et al., "Reduction of Scar Formation in Full-Thickness Wounds with topical Celecoxib Treatment," Wound Repair Regen., Jan-Feb 2003, 11(1):25-34.
Xi et al., "15-Hydroxyeicosatreinoic acid (15-HETrE) suppresses epidermal hyperproliferation via the modulation of nuclear transcription factor (AP-1) and apoptosis," Arch. Dermatol. Res. (2000) 292:379-403.
Xue et al., "Optimization of Synthetic Conditions for the Preparation of Dihomo-gamma-Linolenic Acid from gamma-Linolenic Acid," Journ Amer. Oil Chemists' Soc., Jan 2009, vol. 86, Issue 1, pp. 77-82.
Ziboh et al., "Dihomo-gamma-linolenic acid/15-hydroxyeicosatrienoic acid in skin inflammatory and proliferative processes," pp. 198-206 (2001).
Ziboh et al., "Metabolism of Polyunsaturated Fatty Acids by Skin Epiderman Enzymes: Generation of Antiinflammatory and Antiproliferative Metabolites," Am. J. Clin. Nutr. 2000; 71(suppl):361S-6S.
Zulfakar, M. H. et al.; "Is there a role for topically delivered eicosapentaenoic acid in the treatment of psoriasis"; Eur J Dermatol, 2007, vol. 17, No. 4, pp. 284-291.

* cited by examiner

PHARMACEUTICAL COMPOSITIONS COMPRISING DGLA, 15-HEPE, AND/OR 15-HETRE AND METHODS OF USE THEREOF

PRIORITY CLAIM

This application is a continuation of U.S. Ser. No. 13/478,982, filed May 23, 2012, now U.S. Pat. No. 8,293,790, which claims priority to U.S. Provisional Patent Application Ser. No. 61/549,018, filed Oct. 19, 2011, the entire contents of each of which are incorporated herein by reference.

FIELD

The disclosure generally relates to compositions comprising fatty acids including, for example, DGLA, 15-OHEPA and/or 15-HETrE for the treatment of disease and/or disorders such as acne or atopic dermatitis.

BACKGROUND

There are over a dozen subtypes of acne. Most types of acne are caused by environmental exposure, chemical exposure, physical trauma or abrasion of the skin, or sensitivity to hormone levels. One type, acne vulgaris, and related forms of acne including, for example, acne necrotica, has been linked to bacterial infection by *Propionibacterium acnes*. Presently, there exist numerous regimens for the treatment of acne including topical application of creams comprising benzoyl peroxide. However, such creams are not always effective at reducing the growth of bacteria and ameliorating the clinical manifestation of the condition. Additionally, current regimens are limited in dose strength due to side effects. Accordingly, there exists a need for compositions that are more effective in the treatment of acne.

SUMMARY

The present disclosure provides compositions comprising fatty acids agents including, for example, DGLA, 15-OHEPA and/or 15-HETrE, used singly, in combination and/or in combination with anti-bacterial agents for the treatment of disease and/or disorders such as acne or atopic dermatitis.

The present disclosure also provides methods for treating or preventing acne in a subject in need thereof comprising administering to the subject a pharmaceutical composition comprising a therapeutically effective amount of DGLA, 15-OHEPA, or 15-HETrE or combinations thereof. In some embodiments, the pharmaceutical composition comprises about 0.1 wt. % to about 20 wt. % of DGLA, 15-OHEPA, or 15-HETrE.

In some embodiments, the pharmaceutical composition comprises one or more pharmaceutically acceptable excipients.

In some embodiments, the pharmaceutical composition comprising DGLA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-OHEPA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-HETrE further includes a therapeutically effective amount of adapalene. In some embodiments, the pharmaceutical composition comprises about 0.05% to about 0.3 wt. % of adapalene.

In some embodiments, the step of administering comprises topically applying the composition to an area of the skin afflicted with acne lesions. In some embodiments, the area of the skin afflicted with acne lesions is washed prior to application of the pharmaceutical composition. In some embodiments, the acne lesions are inflammatory type and/or non-inflammatory type lesions.

In some embodiments, applying the composition results in about a 10%, 20%, 30%, 40%, 50%, 60%, 70%, 80%, 90% or more reduction in number of acne lesions.

In some embodiments, the acne is associated with *Propionibacterium acnes*.

In some embodiments, the pharmaceutical composition is administered to the subject once a day, twice a day, or three times a day.

In some embodiments, the pharmaceutical composition is a cream, lotion, gel or emulsion.

In some embodiments, the subject previously exhibited acne lesions.

The present disclosure also provides methods of treating or preventing acne vulgaris or acne necrotica or acne rosacea in a subject in need thereof comprising administering to the subject a pharmaceutical composition comprising a therapeutically effective amount of DGLA. In some embodiments, the pharmaceutical composition comprises about 0.1% to about 20 wt. % of DGLA.

In some embodiments, the pharmaceutical composition comprising DGLA further includes a therapeutically effective amount of benzoyl peroxide. In some embodiments, the pharmaceutical composition comprises about 1.25% to about 10 wt. % of benzoyl peroxide.

In some embodiments, the step of administering comprises topically applying the composition to an area of the skin afflicted with acne lesions. In some embodiments, the area of the skin afflicted with acne lesions is first washed prior to application of the pharmaceutical composition.

In some embodiments, the acne lesions are inflammatory type and/or non-inflammatory type lesions.

In some embodiments, the composition reduces about 10%, 20%, 30%, 40%, 50%, 60%, 70%, 80%, 90% or more of the acne lesions.

In some embodiments, the acne is associated with *Propionibacterium acnes*.

In some embodiments, the pharmaceutical composition is administered to the subject once a day, twice a day, or three times a day.

In some embodiments, the pharmaceutical composition is a cream, lotion, gel or emulsion.

In some embodiments, the subject previously exhibited acne lesions.

The present disclosure also provides compositions for use in treating acne comprising a therapeutically effective amount of DGLA, 15-OHEPA, or 15-HETrE. In some embodiments, the composition comprises about 0.1% to about 20 wt. % of DGLA, 15-OHEPA, or 15-HETrE.

In some embodiments, the composition comprising DGLA further includes a therapeutically effective amount of benzoyl peroxide. In some embodiments, the composition comprises about 1.25% to about 10 wt. % of benzoyl peroxide.

In some embodiments, the pharmaceutical composition comprising 15-OHEPA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-HETrE further includes a therapeutically effective amount of adapalene. In some embodiments, the pharmaceutical composition comprises about 0.05% to about 0.3 wt. % of adapalene.

The present disclosure also provides methods for improving the antimicrobial activity of an agent used in the treatment of acne comprising adding a composition comprising one or more of DGLA, 15-OHEPA, or 15-HETrE to the agent. In some embodiments, the composition comprises about 0.1% to about 20 wt. % of DGLA, 15-OHEPA, or 15-HETrE.

In some embodiments, the composition comprising DGLA further includes a therapeutically effective amount of benzoyl peroxide. In some embodiments, the composition comprises about 1.25% to about 10 wt. % of benzoyl peroxide.

In some embodiments, the composition comprising 15-OHEPA further includes a therapeutically effective amount of benzoyl peroxide. In some embodiments, the composition comprises about 1.25% to about 10 wt. % of benzoyl peroxide.

In some embodiments, the composition comprising 15-HETrE further includes a therapeutically effective amount of adapalene. In some embodiments, the composition comprises about 0.05% to about 0.3 wt. % of adapalene.

The present disclosure also provides methods of inhibiting *Propionibacterium acnes* including, for example, its reproduction, growth or recolonization, comprising contacting *Propionibacterium acnes* with a composition comprising DGLA, 15-OHEPA, or 15-HETrE. In some embodiments, the composition comprises about 0.1% to about 20 wt. % of DGLA, 15-OHEPA, or 15-HETrE.

In some embodiments, the pharmaceutical composition comprising DGLA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-OHEPA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-HETrE further includes a therapeutically effective amount of adapalene. In some embodiments, the pharmaceutical composition comprises about 0.05% to about 0.3 wt. % of adapalene.

The present disclosure also provides a product for use in the treatment of acne comprising a container; and a pharmaceutical composition comprising a therapeutically effective amount of DGLA, 15-OHEPA, or 15-HETrE, releasably confined inside the container. In some embodiments, the pharmaceutical composition comprises about 0.1% to about 20 wt. % of DGLA, 15-OHEPA, or 15-HETrE.

In some embodiments, the pharmaceutical composition comprising DGLA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-OHEPA further includes a therapeutically effective amount of benzoyl peroxide. In some embodiments, the pharmaceutical composition comprises about 1.25% to about 10 wt. % of benzoyl peroxide.

In some embodiments, the pharmaceutical composition comprising 15-HETrE further includes a therapeutically effective amount of adapalene. In some embodiments, the pharmaceutical composition comprises about 0.05% to about 0.3 wt. % of adapalene.

The present disclosure also provides methods for treating or preventing atopic dermatitis in a subject in need thereof comprising administering to the subject a pharmaceutical composition comprising a therapeutically effective amount of DGLA, 15-OHEPA, or 15-HETrE.

In some embodiments, the methods may further comprise administering to the subject a steroid. In some embodiments, the steroid is a corticosteroid such as hydrocortisone, prednicarbate, fluticasone and derivatives thereof, or mometasone and derivatives thereof.

In some embodiments, the subject is administered the therapeutically effective amount of DGLA, 15-OHEPA, or 15-HETrE and the steroid concomitantly.

In some embodiments, the pharmaceutical composition comprises about 0.1 wt. % to about 20 wt. % of DGLA, 15-OHEPA, or 15-HETrE.

In some embodiments, the pharmaceutical compositions described herein comprise one or more of steareth-2, steareth-21, cetyl alcohol, ascorbyl palmitate, about a-tocopherol, medium-chain triglycerides (e.g., Crodamol GTCC), myristyl myristate, isopropryl palmitate, glycerin, phenoxyethanol, ascorbic acid, carbomer, xanthan gum, liquid soy lecithin, and/or Mild Care 345 fragrance.

In some embodiments, the step of administering comprises topically applying the composition to an area of the skin afflicted with atopic dermatitis.

In some embodiments, the area of the skin afflicted with atopic dermatitis is first washed prior to application of the pharmaceutical composition.

In some embodiments, the pharmaceutical composition is administered to the subject once a day, twice a day, or three times a day.

In some embodiments, the pharmaceutical composition is a cream.

The present disclosure also provides methods for improving the efficacy of an agent used in the treatment of atopic dermatitis comprising adding a therapeutically effective amount of DGLA, 15-OHEPA, or 15-HETrE to the agent.

In some embodiments, about 0.1% to about 20 wt. % of DGLA, 15-OHEPA, or 15-HETrE is added to the agent.

The present disclosure also provides methods for reducing the efficacious dose of an agent used in the treatment of atopic dermatitis comprising adding a therapeutically effective amount of DGLA, 15-OHEPA, or 15-HETrE to the agent.

In some embodiments, about 0.1% to about 20 wt. % of DGLA, 15-OHEPA, or 15-HETrE is added to the agent.

These and other embodiments of the invention are described in further detail below.

DETAILED DESCRIPTION

The present disclosure provides compositions (e.g., pharmaceutical compositions) and formulations that comprise fatty acid agents including, for example, DGLA, 15-OHEPA and/or 15-HETrE. Such agents have been found to reduce including, inhibit, the growth of bacteria such as *Propionibacterium acnes* (*P. Acnes*). Furthermore, the inventors have found that, in many cases, the use of these fatty acid agents in combination with existing antibacterial agents (e.g., nicotinamide, benzoyl peroxide, adapalene, or metronidazole) provides additional reduction in the growth of bacteria compared to each agent used singly. Given their capacity to reduce, inhibit and/or prevent, the growth of bacteria, the compositions and formulations disclosed herein may be used in the treatment of disease and/or disorders associated with the growth of bacteria (e.g. acne).

The present disclosure provides compositions comprising fatty acids including, for example, DGLA, 15-OHEPA and/or 15-HETrE in free acid or derivative form, used singly or in combination with antibacterial agents including, for example, nicotinamide, benzoyl peroxide, adapalene, or metronidazole. In some embodiments, the compositions comprise about 0.1 wt. % to about 20 wt. % of DGLA, 15-OHEPA, or 15-HETrE or derivative thereof. Contemplated combinations include, without limitation, DGLA and benzoyl peroxide, 15-OHEPA and benzoyl peroxide, 15 HETrE benzoyl peroxide and 15-HETrE and adapalene. In some embodiments, a composition comprising DGLA includes a therapeutically effective amount (e.g., about 1.25% to about 10 wt. %) of benzoyl peroxide. In some embodiments, a composition comprising 15-OHEPA includes a therapeutically effective amount (e.g., about 0.05% to about 0.3 wt. %) of adapalane peroxide. In some embodiments, a composition comprising 15-HETrE includes a therapeutically effective amount (e.g., about 0.05% to about 0.3 wt. %) of adapalene.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Dihomo-gamma-linolenic acid, also known as cis-8,11,14-eicosatrienoic acid or C 20:3ω6 ("DGLA"), is the elongation product of gamma-linolenic acid, also referred to as gamoleic acid or C18:3ω6 ("GLA"). GLA is a component of natural oils from a variety of plants such as Echium, blackcurrant, borage, evening primrose, hackelia, trichodesma, and buglossoides, to name a few. As used herein, the term "DGLA" refers to DGLA free acid (e.g., cis-8,11,14-eicosatrienoic acid) and/or a pharmaceutically acceptable ester, derivative, conjugate or salt thereof, or mixtures of any of the foregoing. In some embodiments, DGLA is in the form of a $C_{1-4}$ alkyl ester such as methyl ester or ethyl ester form.

15-Hydroxy-eicosa-5,8,11,13,17-pentaenoic acid ("15-OHEPA" or "15-HEPE") is a derivative of EPA. As used herein, the term "15-OHEPA" refers to 15-OHEPA in its free acid form (e.g, 15-hydroxy-eicosa-5,8,11,13,17-pentaenoic acid) and/or a pharmaceutically acceptable ester, derivative, conjugate or salt thereof, or mixtures of any of the foregoing. In some embodiments, the 15-OHEPA is in the form of a $C_{1-4}$ alkyl ester such as methyl ester or ethyl ester form.

15-Hydroxy-eicosa-8(Z),11(Z),13(E)-trienoic acid ("15-HETrE") is a derivative of DGLA. As used herein, the term "15-HETrE" refers to 15-HETrE in its free acid form (e.g., 15-hydroxy-eicosa-8(Z),11(Z),13(E)-trienoic acid) and/or a pharmaceutically acceptable ester, derivative, conjugate or salt thereof, or mixtures of any of the foregoing.

As used herein, the terms "DGLA derivative" and "derivative of DGLA" refer to compounds formed from the chemical conversion of DGLA including, without limitation, 15-HETrE, and esters, derivatives, conjugates or salts thereof, or mixtures of any of the foregoing. One of skill in the art will readily recognize from the chemical structure and other properties whether a given compound is a DGLA derivative.

In one embodiment, DGLA, 15-OHEPA, and/or 15-HETrE is deodorized prior to use in a method or composition as disclosed herein. In one embodiment, crude DGLA, 15-OHEPA, and/or 15-HETrE is mixed with silica and charcoal. In one embodiment, the silica and charcoal are in a ratio of about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, the ratio of DGLA (or 15-OHEPA or 15-HETrE) to silica/charcoal is about 1:1 to about 50:1, for example about 1:1, about 2:1, about 3:1, about 4:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 45:1, or about 50:1. In one embodiment, crude DGLA, 15-OHEPA, and/or 15-HETrE has been deodorized by filtering over a CELITE filter. In another embodiment, lecithin is used in the deodorizing of the fatty acids.

In various embodiments, the invention provides pharmaceutical compositions, for example topically deliverable compositions, comprising one or more of DGLA, 15-OHEPA, 15-HETrE or mixtures thereof.

In one embodiment, the present disclosure provides pharmaceutical compositions comprising, for example, an amount (e.g., a therapeutically effective amount) of DGLA, 15-OHEPA, 15-HETrE, or a combination thereof. In one embodiment, the pharmaceutical composition comprises about 0.1 wt. % to about 20 wt. % of the DGLA, 15-OHEPA, 15-HETrE, or a combination thereof, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt. %, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt. %, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, or about 20 wt % of the DGLA, 15-OHEPA, 15-HETrE, or a combination thereof.

In one embodiment, the pharmaceutical composition further comprises an additional active agent. In one embodiment, the pharmaceutical composition comprises an amount of the additional active agent that is less than the generally recognized therapeutically effective amount for that agent. In one embodiment, the pharmaceutical composition comprises an amount of the additional active agent that is equal to or greater than the generally recognized therapeutically effective amount for that agent. In one embodiment, the additional active agent has not previously been recognized as effective in the treatment or prevention of acne. In another embodiment, the additional active agent is approved for use in the treatment or prevention of acne. In one embodiment, the additional active agent is a peroxide.

In one embodiment, the additional active agent is benzoyl peroxide. In one embodiment, the pharmaceutical composition comprises an amount of benzoyl peroxide that is less than the generally recognized therapeutically effective amount. In one embodiment, the pharmaceutical composition comprises an amount of benzoyl peroxide that is equal to or greater than the generally recognized therapeutically effective amount. In one embodiment, the pharmaceutical composition comprises about 2.5 wt. % to about 10 wt. % of benzoyl peroxide, for example about 1.25 wt. %, about 1.3 wt. %, about 1.4 wt. %, about 1.5 wt. %, about 1.6 wt %, about 1.7 wt %, about 1.7 wt %, about 1.9 wt. %, about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, or about 10 wt. % of benzoyl peroxide.

In one embodiment, the additional active agent is adapalene (6-[3-(1-adamantyl)-4-methoxyphenyl]-2-naphthoic acid). In one embodiment, the pharmaceutical composition comprises an amount of adapalene that is less than the generally recognized therapeutically effective amount. In one embodiment, the pharmaceutical composition comprises an amount of the adapalene that is equal to or greater than the generally recognized therapeutically effective amount. In one embodiment, the pharmaceutical composition comprises about 0.05 wt. % to about 0.3 wt. % of adapalene, for example about 0.05 wt. %, about 0.06 wt. %, about 0.07 wt %, about 0.08% about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, or about 0.3 wt. % of adapalene.

Any pharmaceutically acceptable excipient known to those of skill in the art may be used in pharmaceutical compositions according to the present disclosure. Any excipient selected for use in the therapeutic and cosmetic compositions should be pharmaceutically and/or cosmetically acceptable and appropriate for the form in which the therapeutic composition will be used, e.g., cream, gel, milk, oil, lotion, and the like. Preferably, the excipient has an affinity for the skin, is well tolerated, and stable when used in an amount adequate to provide the desired consistency and ease of application. By way of example only, a pharmaceutical composition according to the present disclosure may comprise one or more of: surfactants, preservatives, flavouring agents, co-solvents, viscosity aids, suspension aids, and lipophilic phases.

In one embodiment, the pharmaceutical composition comprises about 0.5 wt. % to about 5 wt. % of a surfactant such as an ethoxylated natural fatty alcohol (e.g., Steareth-2), for example, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, about 3.05 wt. %, about 3.1 wt. %, about 3.15 wt. %, about 3.2 wt. %, about 3.25 wt. %, about 3.3 wt. %, about 3.35 wt. %, about 3.4 wt. %, about 3.45 wt. %, about 3.5 wt. %, about 3.55 wt. %, about 3.6 wt. %, about 3.65 wt. %, about 3.7 wt. %, about 3.75 wt. %, about 3.8 wt. %, about 3.85 wt. %, about 3.9 wt. %, about 3.95 wt. %, about 4 wt. %, about 4.05 wt. %, about 4.1 wt. %, about 4.15 wt. %, about 4.2 wt. %, about 4.25 wt. %, about 4.3 wt. %, about 4.35 wt. %, about 4.4 wt. %, about 4.45 wt. %, about 4.5 wt. %, about 4.55 wt. %, about 4.6 wt. %, about 4.65 wt. %, about 4.7 wt. %, about 4.75 wt. %, about 4.8 wt. %, about 4.85 wt. %, about 4.9 wt. %, about 4.95 wt. %, about 5 wt. % of the surfactant. In one embodiment the surfactant is Steareth-2 (e.g., BRIJ S2, Croda International plc).

In one embodiment, the pharmaceutical composition comprises about 0.5 wt. % to about 5 wt. % of an emulsifier such as a polyoxyethylene fatty ether (e.g., Steareth-21), for example, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.05 wt. %, about 1.1 wt. %, about 1.15 wt. %, about 1.2 wt. %, about 1.25 wt. %, about 1.3 wt. %, about 1.35 wt. %, about 1.4 wt. %, about 1.45 wt. %, about 1.5 wt. %, about 1.55 wt. %, about 1.6 wt. %, about 1.65 wt. %, about 1.7 wt. %, about 1.75 wt. %, about 1.8 wt. %, about 1.85 wt. %, about 1.9 wt. %, about 1.95 wt. %, about 2 wt. %, about 2.05 wt. %, about 2.1 wt. %, about 2.15 wt. %, about 2.2 wt. %, about 2.25 wt. %, about 2.3 wt. %, about 2.35 wt. %, about 2.4 wt. %, about 2.45 wt. %, about 2.5 wt. %, about 2.55 wt. %, about 2.6 wt. %, about 2.65 wt. %, about 2.7 wt. %, about 2.75 wt. %, about 2.8 wt. %, about 2.85 wt. %, about 2.9 wt. %, about 2.95 wt. %, about 3 wt. %, about 3.05 wt. %, about 3.1 wt. %, about 3.15 wt. %, about 3.2 wt. %, about 3.25 wt. %, about 3.3 wt. %, about 3.35 wt. %, about 3.4 wt. %, about 3.45 wt. %, about 3.5 wt. %, about 3.55 wt. %, about 3.6 wt. %, about 3.65 wt. %, about 3.7 wt. %, about 3.75 wt. %, about 3.8 wt. %, about 3.85 wt. %, about 3.9 wt. %, about 3.95 wt. %, about 4 wt. %, about 4.05 wt. %, about 4.1 wt. %, about 4.15 wt. %, about 4.2 wt. %, about 4.25 wt. %, about 4.3 wt. %, about 4.35 wt. %, about 4.4 wt. %, about 4.45 wt. %, about 4.5 wt. %, about 4.55 wt. %, about 4.6 wt. %, about 4.65 wt. %, about 4.7 wt. %, about 4.75 wt. %, about 4.8 wt. %, about 4.85 wt. %, about 4.9 wt. %, about 4.95 wt. %, about 5 wt. % of the emulsifier. In one embodiment the emulsifier is Steareth-21 (e.g., BRIJ S721, Croda International plc).

In one embodiment, the pharmaceutical composition comprises a stabilizer such as a cetyl alcohol or a saturated cetyl alcohol (e.g., cetyl alcohol). In one embodiment, the pharmaceutical composition comprises about 0.1 wt. % to about 5 wt. % of a stabilizer, for example about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.01 wt. %, about 1.02 wt. %, about 1.03 wt. %, about 1.04 wt. %, about 1.05 wt. %, about 1.06 wt. %, about 1.07 wt. %, about 1.08 wt. %, about 1.09 wt. %, about 1.1 wt. %, about 1.11 wt. %, about 1.12 wt. %, about 1.13 wt. %, about 1.14 wt. %, about 1.15 wt. %, about 1.16 wt. %, about 1.17 wt. %, about 1.18 wt. %, about 1.19 wt. %, about 1.2 wt. %, about 1.21 wt. %, about 1.22 wt. %, about 1.23 wt. %, about 1.24 wt. %, about 1.25 wt. %, about 1.26 wt. %, about 1.27 wt. %, about 1.28 wt. %, about 1.29 wt. %, about 1.3 wt. %, about 1.31 wt. %, about 1.32 wt. %, about 1.33 wt. %, about 1.34 wt. %, about 1.35 wt. %, about 1.36 wt. %, about 1.37 wt. %, about 1.38 wt. %, about 1.39 wt. %, about 1.4 wt. %, about 1.41 wt. %, about 1.42 wt. %, about 1.43 wt. %, about 1.44 wt. %, about 1.45 wt. %, about 1.46 wt. %, about 1.47 wt. %, about 1.48 wt. %, about 1.49 wt. %, about 1.5 wt. %, about 1.51 wt. %, about 1.52 wt. %, about 1.53 wt. %, about 1.54 wt. %, about 1.55 wt. %, about 1.56 wt. %, about 1.57 wt. %, about 1.58 wt. %, about 1.59 wt. %, about 1.6 wt. %, about 1.61 wt. %, about 1.62 wt. %, about 1.63 wt. %, about 1.64 wt. %, about 1.65 wt. %, about 1.66 wt. %, about 1.67 wt. %, about 1.68 wt. %, about 1.69 wt. %, about 1.7 wt. %, about 1.71 wt. %, about 1.72 wt. %, about 1.73 wt. %, about 1.74 wt. %, about 1.75 wt. %, about 1.76 wt. %, about 1.77 wt. %, about 1.78 wt. %, about 1.79 wt. %, about 1.8 wt. %, about 1.81 wt. %, about 1.82 wt. %, about 1.83 wt. %, about 1.84 wt. %, about 1.85 wt. %, about 1.86 wt. %, about 1.87 wt. %, about 1.88 wt. %, about 1.89 wt. %, about 1.9 wt. %, about 1.91 wt. %, about 1.92 wt. %, about 1.93 wt. %, about 1.94 wt. %, about 1.95 wt. %, about 1.96 wt. %, about 1.97 wt. %, about 1.98 wt. %, about 1.99 wt. %, about 2 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt % of the stabilizer. In one embodiment, the stabilizer is cetyl alcohol (e.g., Crodacol C95 EP, Croda International plc).

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt.

%, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

In one embodiment the antioxidant is ascorbyl palmitate. In one embodiment the antioxidant is α-tocopherol. In one embodiment the antioxidant is ascorbic acid. In one embodiment the antioxidant is idebenone. In one embodiment, the antioxidant is ubiquinone. In one embodiment, the antioxidant is ferulic acid. In one embodiment, the antioxidant is coenzyme Q10. In one embodiment, the antioxidant is lycopene. In one embodiment, the antioxidant is green tea. In one embodiment, the antioxidant is catechins. In one embodiment, the antioxidant is epigallocatechin 3-gallate (EGCG). In one embodiment, the antioxidant is green tea polyphenols (GTP). In one embodiment, the antioxidant is silymarin. In one embodiment, the antioxidant is coffeeberry. In one embodiment, the antioxidant is resveratrol. In one embodiment, the antioxidant is grape seed. In one embodiment, the antioxidant is pomegranate extracts. In one embodiment, the antioxidant is genisten. In one embodiment, the antioxidant is pycnogenol. In one embodiment, the antioxidant is niacinamide. In one embodiment, the pharmaceutical composition comprises about 0.01 wt. % to about 0.5 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.1 wt. % to about 0.3 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.3 wt. % to about 0.5 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, and niacinamide. In one embodiment, the pharmaceutical composition comprises about 0.45 wt. % of one or more antioxidants selected from the group consisting of ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, COFFEEBERRY, resveratrol, grape seed, pomegranate extracts, genisten, pycnogenol, and niacinamide. In one embodiment, the pharmaceutical composition comprises about 0.05 wt. % of idebenone. In one embodiment, the pharmaceutical composition comprises about 0.05 wt. % to about 1 wt. % of ubiquinone, for example about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. % of ubiquinone. In one embodiment, the pharmaceutical composition comprises about 0.1 wt. % to about 1 wt. % of ferulic acid, for example about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, or about 1 wt. % of ferulic acid. In one embodiment, the pharmaceutical composition comprises about 0.01 wt. % to about 0.5 wt. % of ascorbyl palmitate, about 0.01 wt. % to about 0.5 wt. % of α-tocopherol, and about 0.01 wt. % to about 0.5 wt. % of ascorbic acid. In one embodiment the pharmaceutical composition comprises about 0.1 wt. % to about 0.3 wt. % of ascorbyl palmitate, about 0.1 wt. % to about 0.3 wt. % of α-tocopherol, and about 0.05 wt. % to about 0.2 wt. % of ascorbic acid. In one embodiment the pharmaceutical composition comprises about 0.2 wt. % of ascorbyl palmitate, about 0.15 wt. % of α-tocopherol, and about 0.1 wt. % of ascorbic acid.

In one embodiment, the pharmaceutical composition comprises one or more emollients such as a fully saturated triglyceride (e.g., medium-chain triglycerides such as Crodamol GTCC, Croda International plc), myristyl myristate, isopropyl palmitate, and glycerin. In one embodiment, the pharmaceutical composition comprises about 0.5 wt. % to about 20 wt. % of an emollient, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt. %, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt. %, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, or about 20 wt. % of an emollient. In one embodiment, the pharmaceutical composition comprises about 0.5 wt. % to about 5 wt. % of any one emollient. In one embodiment, the one or more emollients are selected from the group consisting of medium-chain triglycerides (e.g., Crodamol GTCC, Croda International plc), myristyl myristate, isopropryl palmitate, and glycerin.

In one embodiment, the pharmaceutical composition comprises medium-chain triglycerides (e.g., Crodamol GTCC), myristyl myristate, isopropryl palmitate and glycerin in a combined amount of about 0.5 wt. to about 20 wt. %. In one embodiment, the pharmaceutical composition comprises about 0.5 wt. % to about 5 wt. % of medium-chain triglycerides (e.g., Crodamol GTCC), for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of medium-chain triglycerides (e.g., Crodamol GTCC). In one embodiment, the pharmaceutical composition comprises about 0.5 wt. % to about 5 wt. % of myristyl myristate, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of myristyl myristate.

In one embodiment, the pharmaceutical composition comprises about 0.5 wt. % to about 8 wt. % of isopropryl palmitate, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, or about 8 wt. % of isopropryl palmitate.

In one embodiment, the pharmaceutical composition comprises about 0.5 wt. % to about 5 wt. % of glycerin, for example about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of glycerin. in one embodiment, the pharmaceutical composition comprises about 2 wt. % of medium-chain triglycerides (e.g., Crodamol GTCC), about 2 wt. % of myristyl myristate (e.g., Crodamol MM, Croda International plc), about 4 wt. % of isopropryl palmitate (e.g., Crodamol IPP, Croda International plc), and about 1 wt. % of glycerin.

In one embodiment, the pharmaceutical composition comprises a preservative such as phenoxyethanol. In one embodiment, the pharmaceutical composition comprises about 0.1 wt. % to about 5 wt. % of a preservative, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of a preservative. In one embodiment, the preservative is phenoxyethanol. In one embodiment, the pharmaceutical composition comprises about 0.5 wt. % to about 5 wt. % of phenoxyethanol. In one embodiment, the pharmaceutical composition comprises about 0.5 wt. % to about 2 wt. % of phenoxyethanol. In one embodiment, the pharmaceutical composition comprises about 1 wt. % of phenoxyethanol.

In one embodiment, the pharmaceutical composition comprises one or more thickeners, such as a cross-linked polymer (e.g., a cross-linked acrylic acid polymer such as carbomer, available commercially as Carbopol ETD2020NF, Lubrizol Corp.), a polysaccharide (e.g., a xanthan gum such as CPKelko's Keltrol 11K). In one embodiment, the pharmaceutical composition comprises about 0.1 wt. % to about 5 wt. % of one or more thickeners, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of one or more thickeners. In one embodiment, the one or more thickeners is one or more of a cross-linked acrylic acid polymer and a polysaccharide. In one embodiment, the one or more thickeners are Carbopol ETD2020NF and Keltrol 11K. In one embodiment, the pharmaceutical composition comprises about 0.1 wt. % to about 5 wt. % of Carbopol ETD2020NF and about 0.1 wt. % to about 5 wt. % of Keltrol 11K. In one embodiment, the pharmaceutical composition comprises about 0.5 wt. % to about 1 wt. % of Carbopol ETD2020NF and about 0.2 wt. % to about 1 wt. % of Keltrol 11K. In one embodiment, the pharmaceutical composition comprises about 0.8 wt. % of Carbopol ETD2020NF and about 0.4 wt. % of Keltrol 11K.

In one embodiment, the pharmaceutical composition comprises one or more texturizers such as a lecithin (e.g., a liquid soy lecithin such as Leciprime 1400 IPM, Cargill, Inc.). In one embodiment, the pharmaceutical composition comprises about 0.1 wt. % to about 5 wt. % of one or more texturizers, for example about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, or about 5 wt. % of one or more texturizers. In one embodiment, the one or more texturizers comprise Leciprime 1400 IPM. In one embodiment, the pharmaceutical composition comprises about 0.1 wt. % to about 5 wt. % of Leciprime 1400 IPM. In one embodiment, the pharmaceutical composition comprises about 0.2 wt. % to about 1 wt. % of Leciprime 1400 IPM. In one embodiment, the pharmaceutical composition comprises about 0.5 wt. % of Leciprime 1400 IPM.

In one embodiment, the pharmaceutical composition comprises one or more fragrances such as Floral Spa 760, Sensual Wood 138 or Mild Care 345. In one embodiment, the pharmaceutical composition comprises about 0.01 wt. % to about 0.5 wt. % of one or more fragrances, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, or about 0.5 wt. % of one or more fragrances. In one embodiment, the pharmaceutical composition comprises about 0.01 wt. % to about 0.5 wt. % of Mild Care 345 fragrance. In one embodiment, the pharmaceutical composition comprises about 0.01 wt. % to about 0.1 wt. % of Mild Care 345 fragrance. In one embodiment, the pharmaceutical composition comprises about 0.01 wt. % to about 0.05 wt. % of Mild Care 345 fragrance. In one embodiment, the pharmaceutical composition comprises about 0.05 wt. % of Mild Care 345 fragrance.

In one embodiment, the pharmaceutical composition comprises: about 0.5 wt. % to about 20 wt. % of one or more of DGLA, 15-OHEPA, and 15-HETrE; optionally about 1.25 wt. % to about 10 wt. % of benzoyl peroxide; optionally about 0.1 wt. % to about 0.3 wt. of adapalene; about 0.5 wt. % to about 5 wt. % of one or more surfactants; about 0.5 wt. % to about 5 wt. % of one or more emulsifiers; about 0.05 wt. % to about 5 wt. % of one or more stabilizers; about 0.01 wt. % to about 2 wt. % of one or more antioxidants; about 0.5 wt. % to about 20 wt. % of one or more emollients; about 0.1 wt. % to about 5 wt. % of one or more preservatives; about 0.1 wt. % to about 5 wt. % of one or more thickeners; about 0.1 wt. % to about 5 wt. % of one or more texturizers; and about 0.01 wt. % to about 0.5 wt. % of one or more fragrances.

In one embodiment, the pharmaceutical composition comprises: about 0.1 wt. % to about 20 wt. % of one or more of DGLA, 15-OHEPA, and 15-HETrE; optionally about 1.25 wt. % to about 10 wt. % of benzoyl peroxide; optionally about 0.05 wt. % to about 0.3 wt. of adapalene; about 1 wt. % to about 2 wt. % of one or more surfactants; about 1 wt. % to about 2 wt. % of one or more emulsifiers; about 0.1 wt. % to about 1 wt. % of one or more stabilizers; about 0.1 wt. % to about 1 wt. % of one or more antioxidants; about 5 wt. % to about 15 wt. % of one or more emollients; about 0.5 wt. % to about 2 wt. % of one or more preservatives; about 0.5 wt. % to about 2 wt. % of one or more thickeners; about 0.1 wt. % to about 2 wt. % of one or more texturizers; and about 0.01 wt. % to about 0.1 wt. % of one or more fragrances.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 1.65 wt. % of one or more surfactants; about 1.35 wt. % of one or more emulsifiers; about 0.5 wt. % of one or more stabilizers; about 0.45 wt. % of one or more antioxidants; about 9 wt. % of one or more emollients; about 1 wt. % of one or more preservatives; about 1.2 wt. % of one or more thickeners; about 0.5 wt. % of one or more texturizers; and about 0.05 wt. % of one or more fragrances.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 0.5 wt. % to about 5 wt. % of Steareth-2; about 0.5 wt. % to about 5 wt. % of Steareth-21; about 0.1 wt. % to about 5 wt. % of cetyl alcohol; about 0.01 wt. % to about 2 wt. % of a combination of medium-chain triglycerides, myristyl myristate, isopropryl palmitate, and/or glycerin; about 0.5 wt. % to about 20 wt. % of one or more emollients; about 0.1 wt. % to about 5 wt. % of phenoxyethanol; about 0.1 wt. % to about 5 wt. % of a combination of carbomer and/or xanthan gum; about 0.1 wt. % to about 5 wt. % of liquid soy lecithin; and about 0.01 wt. % to about 0.5 wt. % of one or more fragrances.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 1 wt. % to about 2 wt. % of Steareth-2; about 1 wt. % to about 2 wt. % of Steareth-21; about 0.1 wt. % to about 1 wt. % of cetyl alcohol; about 0.1 wt. % to about 1 wt. % of a combination of ascorbyl palmitate, α-tocopherol, and ascorbic acid; about 5 wt. % to about 15 wt. % of a combination of medium-chain triglycerides, myristyl myristate, isopropryl palmitate, and/or glycerin; about 0.5 wt. % to about 2 wt. % of phenoxyethanol; about 0.5 wt. % to about 2 wt. % of a combination of carbomer and/or xanthan gum; about 0.1 wt. % to about 2 wt. % of liquid soy lecithin; and about 0.01 wt. % to about 0.1 wt. % of one or more fragrances.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 1.65 wt. % of Steareth-2; about 1.35 wt. % of Steareth-21; about 0.5 wt. % of cetyl alcohol; about 0.2 wt. % of ascorbyl palmitate; about 0.15 wt. % of α-tocopherol; about 0.1 wt. % of ascorbic acid; about 2 wt. % of medium-chain triglycerides; about 2 wt. % of myristyl myristate; about 4 wt. % of isopropryl palmitate; about 1 wt. % of glycerin; about 1 wt. % of phenoxyethanol, about 0.8 wt. % of carbomer; about 0.4 wt. % of xanthan gum; about 0.5 wt. % of liquid soy lecithin; and about 0.05 wt. % of one or more fragrances.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 0.5 wt. % to about 5 wt. % of BRIJ S2; about 0.5 wt. % to about 5 wt. % of BRIJ 5721; about 0.1 wt. % to about 5 wt. % of Crodacol C95 EP; about 0.01 wt. % to about 2 wt. % of a combination of Crodamol GTCC, Crodamol MM, Crodamol IPP, and/or glycerin; about 0.5 wt. % to about 20 wt. % of one or more emollients; about 0.1 wt. % to about 5 wt. % of phenoxyethanol; about 0.1 wt. % to about 5 wt. % of a combination of Carbopol ETD2020NF and/or Keltrol 11K; about 0.1 wt. % to about 5 wt. % of Leciprime 1400 IPM; and about 0.01 wt. % to about 0.5 wt. % of Mild Care 345 fragrance.

In one embodiment, the pharmaceutical composition comprises: about 0.1 wt. % to about 20 wt. % of one or more of DGLA, 15-OHEPA, and 15-HETrE; optionally about 2.5 wt. % to about 10 wt. % of benzoyl peroxide; optionally about 0.05 wt. % to about 0.3 wt. of adapalene; about 1 wt. % to about 2 wt. % of BRIJ S2; about 1 wt. % to about 2 wt. % of BRIJ 5721; about 0.1 wt. % to about 1 wt. % of Crodacol C95 EP; about 0.1 wt. % to about 1 wt. % of a combination of ascorbyl palmitate, α-tocopherol, and ascorbic acid; about 5 wt. % to about 15 wt. % of a combination of Crodamol GTCC, Crodamol MM, Crodamol IPP, and/or glycerin; about 0.5 wt. % to about 2 wt. % of phenoxyethanol; about 0.5 wt. % to about 2 wt. % of a combination of Carbopol ETD2020NF and/or Keltrol 11K; about 0.1 wt. % to about 2 wt. % of Leciprime 1400 IPM; and about 0.01 wt. % to about 0.1 wt. % of Mild Care 345 fragrance.

In one embodiment, the pharmaceutical composition comprises: about 0.1 wt. % to about 20 wt. % of one or more of DGLA, 15-OHEPA, and 15-HETrE; optionally about 1.25 wt. % to about 10 wt. % of benzoyl peroxide; optionally about 0.05 wt. % to about 0.3 wt. of adapalene; about 1 wt. % to about 2 wt. % of BRIJ S2; about 1 wt. % to about 2 wt. % of BRIJ 5721; about 0.1 wt. % to about 1 wt. % of Crodacol C95 EP; about 0.1 wt. % to about 1 wt. % of a combination of ascorbyl palmitate, α-tocopherol, and ascorbic acid; about 5 wt. % to about 15 wt. % of a combination of Crodamol GTCC, Crodamol MM, Crodamol IPP, and/or glycerin; about 0.5 wt. % to about 2 wt. % of phenoxyethanol; about 0.5 wt. % to about 2 wt. % of a combination of Carbopol ETD2020NF and/or Keltrol 11K; about 0.1 wt. % to about 5 wt. % of Leciprime 1400 IPM; and about 0.01 wt. % to about 0.1 wt. % of Mild Care 345 fragrance.

In one embodiment, the pharmaceutical composition comprises: about 0.1 wt. % to about 20 wt. % of one or more of DGLA, 15-OHEPA, and 15-HETrE; optionally about 1.25 wt. % to about 10 wt. % of benzoyl peroxide; optionally about 0.5 wt. % to about 0.3 wt. of adapalene; about 1.65 wt. % of BRIJ S2; about 1.35 wt. % of BRIJ 5721; about 0.5 wt. % of Crodacol C95 EP; about 0.2 wt. % of ascorbyl palmitate; about 0.15 wt. % of α-tocopherol, about 0.1 wt. % of ascorbic acid; about 2 wt. % Crodamol GTCC; about 2 wt. % of Crodamol MM; about 4 wt. % of Crodamol IPP; about 1 wt. % of glycerin; about 1 wt. % of phenoxyethanol, about 0.8 wt. % of Carbopol ETD2020NF; about 0.4 wt. % of Keltrol 11K; about 0.5 wt. % of Leciprime 1400 IPM; and about 0.05 wt. % of Mild Care 345 fragrance.

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, a composition including, for example, a pharmaceutical composition, as disclosed herein is formulated as an aerosol, a gel, an ointment, a lotion, a cream, a gel stick, a liniment, or a spray.

Such formulations may be stable and comprise an amount (e.g., a therapeutically effective amount) of DGLA, 15-OHEPA, 15-HETrE in combination with one or more antibacterial agents selected from the group consisting of: nicotinamide, benzoyl peroxide, adapalene, and metronidazole.

The present disclosure also provides the disclosed compositions or formulations as a component in a product for use in the treatment of acne. In one embodiment, the product comprises a container and a pharmaceutical composition comprising a therapeutically effective amount of DGLA, 15-OHEPA, 15-HETrE, or a combination thereof. In one embodiment, the pharmaceutical composition comprises from about 0.1 wt. % to about 20 wt. % of DGLA, 15-OHEPA, 15-HETrE, or a combination thereof. In one embodiment, the product comprises a pharmaceutical composition as disclosed herein.

Pharmacokinetics/Pharmacodynamics

The pharmacokinetics and/or pharmacodynamics of the compositions comprising DGLA, 15-OHEPA, or 15-HETrE as disclosed herein may be determined by any method known in the art.

In an embodiment, the pharmacokinetics of a composition comprising DGLA, 15-OHEPA, or 15-HETrE as disclosed herein may be examined using a skin blister technique (see, e.g., Tope, Dermatol Surg 25:348:52 (1999)) to determine the amount of various constituents of the composition that are absorbed through the skin. In an exemplary method, a defined area of the skin is contacted with one or more doses of the compositions at one or more time intervals. Next, epidermal blisters may be made by application of controlled suction to an area of the skin (see, e.g., Kiistala (1968) J. Investig. Dermatol. 50:129-137; Kiistala, et al. (1964) Lancet 1964: 1444-1445; and Schreiner, et al. (1978) Scand. J. Infect. Dis. 14(Suppl.):233-237). Prior to the start of forming a blister on an area of the skin, the area may be hydrated with a warm compress and/or swabbed with 70% isopropanol. Next, a suction apparatus may be placed on the area of the skin and controlled suction applied to with an electric vacuum pump. The vacuum may be increased slowly over a period of time (e.g, 1 min) up to a maximum negative pressure sufficient to form a blister (e.g., 0.3 kg/cm2 (3.104 Pa)). The pressure may be maintained for several hours (e.g., 2 to 3 h) until half-spherical blisters are formed. As soon as the blisters appeared, the vacuum may be released, and the suction chamber apparatus carefully removed without breaking the blister. The blister fluid (e.g., 50-500 µL) may then be aspirated and examined. Samples of blister fluid may be stored at 70° C. until analysis. The concentration of DGLA, 15-OHEPA, or 15-HETrE or other constituents from the disclosed compositions may be determined in blister fluid samples by any method known in the art including, for example, gas chromatography MS (GC/MS), or reverse-phase high-performance liquid chromatography (HPLC).

The compositions comprising DGLA as provided herein deliver DGLA at a mean flux rate of from about 0.1 ng to about 1 mg/cm2/hr at about 2, 4, 6, 8, 12, 24, 48 or 72 hours after administration. The compostions comprising 15-OHEPA as provided herein deliver 15-OHEPA at a mean flux rate of from about 0.1 ng to about 1 mg/cm2/hr at about 2, 4, 6, 8, 12, 24, 48 or 72 hours after administration. The compostions comprising 15-HETrE as provided herein deliver 15-HETrE at a mean flux rate of from about 0.1 ng to about 1 mg/cm2/hr at about 2, 4, 6, 8, 12, 24, 48 or 72 hours after administration.

Methods of Treatment of Diseases and/or Disorders

The compositions and formulations disclosed herein may be used in the treatment of diseases and/or disorders including, for example, disease and/or disorders of the skin such as acne or atopic dermatitis.

Methods are provided herein for treating or preventing acne (e.g., acne vulgaris and/or acne necrotica) in a subject in need thereof comprising administering to the subject a pharmaceutical composition comprising an effective amount including, for example, a therapeutically effective amount (e.g., 0.1 wt. % to about 20 wt. %) of DGLA, 15-OHEPA, or 15-HETrE as described herein.

The term "acne" herein refers to any disease or disorder of the skin that presents with one or more acneiform eruptions such as papules, pustules, cysts, and the like. Non-limiting examples of acne include acne vulgaris, acne necrotica, halogen acne, chloracne, occupational acne, oil acne, tar acne, acne aestivalis, tropical acne, acne cosmetica, pomade acne, acne keloidalis nuchae, acne mechanica, excoriated acne, acne medicamentosa, infantile acne, neonatal acne, acne conglobata, acne fulminans, acne miliaris necrotica, miliaris disseminatus faciei, and, and other skin disorders associated with acneiform eruptions.

In one embodiment, the present disclosure provides a method of treating or preventing acne associated with *P. acnes* in a subject in need thereof. In one embodiment, the method comprises administering to the subject a pharmaceutical composition as disclosed herein, for example a pharmaceutical comprising a therapeutically effective amount of DGLA, 15-OHEPA, 15-HETrE, or a combination thereof. In one embodiment, the pharmaceutical composition comprises from about 0.1 wt. % to about 20 wt. % of DGLA, 15-OHEPA, 15-HETrE, or a combination thereof.

In one embodiment, the present disclosure provides a method of inhibiting *P. acnes* including, for example, its growth, colonization and/or infection in a subject in need thereof. In one embodiment, the method comprises contacting *P. acnes* with a composition as disclosed herein, for example a composition comprising one or more of DGLA, 15-OHEPA, and 15-HETrE. In one embodiment, the composition comprises from about 0.1 wt. % to about 20 wt. % of DGLA, 15-OHEPA, 15-HETrE, or a combination thereof.

In one embodiment, the method further comprises washing an affected area of the skin (and/or to an area of the skin that is generally prone to development of acneiform eruptions) prior to administering the pharmaceutical composition. As used herein, the term "washing" refers generally to any method known to those of skill in the art for cleansing the skin, exfoliating the skin, removing dirt, oil, dead skin cells and the like from the skin, etc.

In one embodiment, the method comprises topically administering the pharmaceutical composition to an area of the skin affected with acne lesions and/or to an area of the skin that is generally prone to development of acne lesions and/or previously had acne lesions.

In one embodiment, the method comprises topically administering the pharmaceutical composition to an area of the skin affected with non-inflammatory acne lesions. In one embodiment, the method comprises topically administering the pharmaceutical composition to an area of the skin affected with inflammatory acne lesions. In one embodiment, the method comprises topically administering the pharmaceutical composition to an area of the skin affected with both non-inflammatory and inflammatory acne lesions.

In one embodiment, the method comprises administering a pharmaceutical composition as disclosed herein once per day, twice per day, three times per day, or more than three times per day.

In one embodiment, upon treatment in accordance with the present disclosure, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the treated area of the skin comprises about 10%, about 20%, about 30%, about 40%, about 50%, about 60%, about 70%, about 80%, about 90%, or greater than about 90% fewer acne lesions than before treatment.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

In another embodiment, the present disclosure provides a method of slowing progression of or promoting regression of acne vulgaris and/or acne necrotica in a subject in need thereof, comprising administering to a subject in need thereof one or more compositions as disclosed herein.

In one embodiment, the present disclosure provides a method of reducing or preventing side effects associated with topical administration of benzoyl peroxide. Administration of high doses of benzoyl peroxide has been associated with redness and irritation of the skin. In one embodiment, a method of reducing side effects associated with topical administration of benzoyl peroxide comprises discontinuing administration of a first pharmaceutical composition comprising benzoyl peroxide and administering to a subject a second pharmaceutical composition as disclosed herein. In one embodiment, the second pharmaceutical composition includes an amount of benzoyl peroxide that is less than the amount of benzoyl peroxide in the first pharmaceutical composition. In one embodiment, the second pharmaceutical composition includes an amount of benzoyl peroxide that is about equal to or equal to the amount of benzoyl peroxide in the first pharmaceutical composition. In one embodiment, the second pharmaceutical composition includes an amount of benzoyl peroxide that is more than the amount of benzoyl peroxide in the first pharmaceutical composition. In one embodiment, the second pharmaceutical composition includes no benzoyl peroxide, essentially no benzoyl peroxide, or substantially no benzoyl peroxide.

In one embodiment, the present disclosure provides a method of reducing or preventing side effects associated with topical administration of retinoids. Administration of high doses of retinoids has been associated with redness and irritation of the skin. In one embodiment, a method of reducing side effects associated with topical administration of retinoids comprises discontinuing administration of a first pharmaceutical composition comprising retinoids and administering to a subject a second pharmaceutical composition as disclosed herein. In one embodiment, the second pharmaceutical composition includes an amount of retinoids that is less than the amount of retinoids in the first pharmaceutical composition. In one embodiment, the second pharmaceutical composition includes an amount of retinoids that is about equal to or equal to the amount of retinoids in the first pharmaceutical composition. In one embodiment, the second pharmaceutical composition includes an amount of retinoids that is more than the amount of retinoids in the first pharmaceutical composition. In one embodiment, the second pharmaceutical composition includes no retinoids, essentially no retinoids, or substantially no retinoids.

In one embodiment, the present disclosure provides a method of reducing production of sebum in at least a portion of a subject's skin. In one embodiment, the method comprises administering to the subject a therapeutically effective amount of a pharmaceutical composition as disclosed herein. In one embodiment, the amount of sebum produced per square inch for a given affected area of the subject's skin after administration of a pharmaceutical composition as disclosed herein is less than, or substantially less than the amount of sebum produced before administration of a pharmaceutical composition as disclosed herein. In one embodiment, treatment according to the present method results in a 10% reduction, about a 20% reduction, about a 30% reduction, about a 40% reduction, about a 50% reduction, about a 60% reduction, about a 70% reduction, about a 80% reduction, about a 90% reduction, or more than a 90% reduction in sebum production for a given area of the subject's skin. In one embodiment, the reduction in sebum production occurs within about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months of the initiation of the treatment method.

In one embodiment, the present disclosure provides a method of reducing acne scarring in at least a portion of a subject's skin. In one embodiment, the method comprises administering to the subject a therapeutically effective amount of a pharmaceutical composition as disclosed herein. In one embodiment, the amount of acne-related scarring per square inch for a given affected area of the subject's skin after administration of a pharmaceutical composition as disclosed herein is less than, or substantially less than the amount of acne-related scarring present in the same area of skin before administration of a pharmaceutical composition as disclosed herein. In one embodiment, treatment according to the present method results in a 10% reduction, about a 20% reduction, about a 30% reduction, about a 40% reduction, about a 50% reduction, about a 60% reduction, about a 70% reduction, about a 80% reduction, about a 90% reduction, or more than a 90% reduction in acne-related scarring for a given area of the subject's skin. In one embodiment, the reduction in acne-related scarring occurs within about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months of the initiation of the treatment method.

The present disclosure also provides methods of improving the antimicrobial activity of an agent used in the treatment of acne. The term "antimicrobial agent" includes antibiotics and antifungals. More specifically, "antimicrobial agents" may include metronidazole, macrolide antibiotics, quinolone antibiotics, penicillins, clindamycin and tetracycline. In one embodiment, the method comprises adding a pharmaceutical comprising one or more of DGLA, 15-OHEPA, and 15-HETrE to the agent. In one embodiment, the agent is one in which no previous antimicrobial activity was appreciated. In one embodiment, the pharmaceutical composition is a pharmaceutical composition as disclosed herein, for example a pharmaceutical composition comprising from about 0.1 wt. % to about 20 wt. % of DGLA, 15-OHEPA, 15-HETrE, or a combination thereof.

The present disclosure also provides methods for reducing including, for example preventing, transepidermal water loss (TEWL). TEWL and diseases or disorders associated with TEWL may be identified by determining a TEWL measurement for at least one portion of the skin (see, e.g., Mundlein et al. (2008) Sensors and Actuators A: Physical 142(1):67-72) and comparing the measurement with that of normal skin (e.g., undiseased). The methods for reducing TEWL may comprise administering to a subject in need thereof a therapeutically effective amount of a pharmaceutical composition as disclosed herein. Such methods may be useful in the treatment and/or prevention of diseases or disorders associated with a disturbance in the stratum corneum (e.g., atopic dermatitis).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Effect of Various Compounds on the Growth of P. Acnes

Several compounds including fatty acids such as DGLA, 15-OHEPA, and 15-HETrE were tested to determine their capacity to inhibit the growth of P. acnes. In an exemplary method, an agar dilution method was used to determine the minimum inhibitory concentration (MIC) of each tested compound. Briefly, the agar dilution method involved preparing a series of concentrations of each compound (e.g., nicotinamide, benzoyl peroxide, adapalene, metronidazole, DGLA, 15-OHEPA, and 15-HETrE) in a Reinforced Clostridial Agar (RCA) media that facilitates growth of P. acnes under anaerobic conditions. An inoculum of P. acnes was prepared by incubation of P. acnes for approximately seven days at 35-37° C. to achieve a ≥1.0 $OD_{600}$ inoculum of P. acnes in RCM broth. A portion of this inoculum was then added to the surface of each plate as a 10 μL spot and incubated at 35-37° C. for 72 hours or more. Growth of P. acnes was then observed and compared to control plates in which no compound has been added, and positive inhibition plates prepared with erythromycin. The growth profile of each colony (spot) was characterized as per the following index: (+++) confluent growth (comparable to control); (++) less confluent growth; (+) marked reduction in growth to multiple tiny, single colonies; and (−) no growth present. The growth of P. acnes in the presence of nicotinamide, benzoyl peroxide, adapalene, metronidazole, DGLA, 15-OHEPA, and 15-HETrE was determined with varying concentrations of the compound (see, Table 2). Next, the MIC was determined as the concentration at which a marked reduction (+) occurs in the appearance of growth on the test plate (as per Clinical and Laboratory Standards Institute M11-A7).

TABLE 2

Effect of Various Compounds on Growth of P. Acnes.

| Nicotinamide | | | | |
|---|---|---|---|---|
| | | Growth Index | | |
| Nicotinamide | | (+++, ++, +, −) | | |
| [mg/mL] | Plate 1 | Plate 2 | Plate 3 | Avg |
| 1 | +++ | +++ | +++ | +++ |
| 5 | +++ | +++ | +++ | +++ |
| 10 | ++ | ++ | ++ | ++ |
| 15 | − | + | + | + |
| 25 | − | − | − | − |

| Benzoyl Peroxide: | | | | |
|---|---|---|---|---|
| | | Growth Index | | |
| | | (+++, ++, +, −) | | |
| BPO [mg/mL] | Plate 1 | Plate 2 | Plate 3 | Avg |
| 0.2 | +++ | +++ | +++ | +++ |
| 0.4 | +++ | +++ | +++ | +++ |
| 0.6 | ++ | +++ | ++ | ++ |
| 0.8 | + | + | + | + |
| 1.0 | − | − | − | − |

TABLE 2-continued

Effect of Various Compounds on Growth of *P. Acnes*.

Adapalene:

| Adapalene [mg/mL] | Growth Index (+++, ++, +, −) | | | |
|---|---|---|---|---|
| | Plate 1 | Plate 2 | Plate 3 | Avg. |
| 0.2 | +++ | +++ | +++ | +++ |
| 0.4 | +++ | +++ | +++ | +++ |
| 0.6 | ++ | ++ | +++ | ++ |
| 0.8 | ++ | ++ | ++ | ++ |

Metronidazole:

| Metronidazole [mg/mL] | Growth Index (+++, ++, +, −) | | | |
|---|---|---|---|---|
| | Plate 1 | Plate 2 | Plate 3 | Avg |
| 0.2 | +++ | +++ | +++ | +++ |
| 0.4 | +++ | +++ | +++ | +++ |
| 0.6 | +++ | +++ | +++ | +++ |
| 0.8 | +++ | +++ | +++ | +++ |
| 1.0 | +++ | ++ | +++ | +++ |

DGLA:

| DGLA [mg/mL] | Growth Index (+++, ++, +, −) | | | |
|---|---|---|---|---|
| | Plate 1 | Plate 2 | Plate 3 | Avg. |
| 0.2 | +++ | +++ | +++ | +++ |
| 0.4 | +++ | +++ | +++ | +++ |
| 0.6 | ++ | − | ++ | + |
| 0.8 | ++ | + | + | + |
| 1.0 | + | + | + | + |

15-OHEPA:

| 15-OHEPA [mg/mL] | Growth Index (+++, ++, +, −) | | | |
|---|---|---|---|---|
| | Plate 1 | Plate 2 | Plate 3 | Avg. |
| 0.010 | +++ | +++ | +++ | +++ |
| 0.025 | +++ | +++ | +++ | +++ |
| 0.050 | +++ | +++ | +++ | +++ |
| 0.075 | + | + | + | + |

15-HETrE:

| 15-HETrE [mg/mL] | Growth Index (+++, ++, +, −) | | | |
|---|---|---|---|---|
| | Plate 1 | Plate 2 | Plate 3 | Avg. |
| 0.00001 | +++ | +++ | +++ | +++ |
| 0.0001 | +++ | +++ | +++ | +++ |
| 0.001 | +++ | +++ | +++ | +++ |
| 0.01 | ++ | +++ | ++ | ++ |

The MIC for DGLA was determined to be >0.4, ≤0.6. Additionally, the MICs for 15-HETrE and 15-OHEPA were determined to be >0.01, ≤0.05 and >0.05, ≤0.075, respectively.

Example 2

Effects of Fatty Acid Compounds in Combination with Other Compounds on the Growth of *P. Acnes*

The compounds tested singly in Example 1 were tested in combination with one another to determine the capacity of the combination to inhibit the growth of *P. acnes*. In an exemplary method, the MIC was determined for each of the combination as described in Example 1. Briefly, test combinations included DGLA with nicotinamide, benzoyl peroxide, adapalene, or metronidazole; 15-HETrE with nicotinamide, benzoyl peroxide, adapalene, or metronidazole; and 15-OHEPA with nicotinamide, benzoyl peroxide, adapalene, or metronidazole. The tables below show the growth of *P. acnes* in the presence of 0.4 or 1.0 mg/mL DGLA with varying concentrations of nicotinamide, benzoyl peroxide, adapalene, or metronidazole (Table 3); the growth of *P. acnes* in the presence of 0.01 or 0.05 mg/mL 15-HETrE with varying concentrations of nicotinamide, benzoyl peroxide, adapalene, or metronidazole (Table 5); and the growth of *P. acnes* in the presence of 0.5 or 0.1 mg/mL 15-OHEPA with varying concentrations of nicotinamide, benzoyl peroxide, adapalene, or metronidazole (Table 7).

TABLE 3

Combinations of Antibacterial Compositions with DGLA

| Nicotinamide [mg/mL] | Growth Index (+++, ++, +, −) | | | |
|---|---|---|---|---|
| | Plate 1 | Plate 2 | Plate 3 | Avg. |
| Nicotinamide + 0.4 mg/mL dGLA (<MIC): | | | | |
| 1 | +++ | +++ | +++ | +++ |
| 5 | +++ | +++ | +++ | +++ |
| 10 | +++ | +++ | +++ | +++ |
| 15 | + | + | + | + |
| Nicotinamide + 1.0 mg/mL dGLA (<MIC): | | | | |
| 1 | +++ | +++ | +++ | +++ |
| 5 | +++ | +++ | +++ | +++ |
| 10 | + | ++ | ++ | ++ |
| 15 | − | − | − | − |

| BPO [mg/mL] | Growth Index (+++, ++, +, −) | | | |
|---|---|---|---|---|
| | Plate 1 | Plate 2 | Plate 3 | Avg. |
| Benzoyl Peroxide + 0.4 mg/mL dGLA (<MIC): | | | | |
| 0.2 | +++ | +++ | +++ | +++ |
| 0.4 | + | − | − | − |
| 0.6 | − | − | − | − |
| 0.8 | − | − | − | − |
| 1.0 | − | − | − | − |
| Benzoyl Peroxide + 1.0 mg/mL dGLA (<MIC): | | | | |
| 0.2 | ++ | ++ | + | ++ |
| 0.4 | − | + | − | − |
| 0.6 | − | − | − | − |
| 0.8 | − | − | − | − |

| Adapalene [mg/mL] | Growth Index (+++, ++, +, −) | | | |
|---|---|---|---|---|
| | Plate 1 | Plate 2 | Plate 3 | Avg. |
| Adapalene + 0.4 mg/mL dGLA (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | +++ | +++ | +++ |
| 1.0 | +++ | +++ | +++ | +++ |
| Adapalene + 1.0 mg/mL dGLA (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | +++ | +++ | +++ |

TABLE 3-continued

Combinations of Antibacterial Compositions with DGLA

| Metronidazole [mg/mL] | Growth Index (+++, ++, +, −) | | | |
|---|---|---|---|---|
| | Plate 1 | Plate 2 | Plate 3 | Avg. |
| Metronidazole + 0.4 mg/mL dGLA (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | ++ | ++ | ++ |
| 1.0 | ++ | ++ | ++ | ++ |
| Metronidazole + 1.0 mg/mL dGLA (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | +++ | ++ | +++ |
| 1.0 | ++ | ++ | ++ | ++ |

DGLA in combination with other compounds including nicotinamide, metranidazole or adapalene did not reduce the growth of P. Acnes below that of DGLA used alone. However, a spike of 0.4 mg/ml DGLA reduced the MIC obtained with benzoyl peroxide from >0.6, ≤0.8 to >0.2, ≤0.4. These results suggest that DGLA and benzoyl peroxide may exhibit synergy since 0.4 mg/ml DGLA has no effect on its own but when it is added to benzoyl peroxide it is able to further decrease the growth rate of P. acnes below that of the DGLA single compound treatment (see, Table 4).

TABLE 4

DGLA Combination Summary

| Compound | MIC (mg/mL) as per P-11-0007 or P-11-0008 Addendum A | MIC (mg/mL) with 0.4 mg/mL dGLA spike** | MIC (mg/mL) with 1.0 mg/mL dGLA spike*** |
|---|---|---|---|
| Metronidazole | >1 | >1 | >1 |
| Nicotinamide | >10, ≤15 | >10, ≤15 | >10, ≤15 |
| BPO | >0.6, ≤0.8 | >0.2, ≤0.4 | >0.2, ≤0.4 |
| Erythromycin | >0.00001, ≤0.00005 | N/App | N/App |
| dGLA | >0.4, ≤0.6** | N/App | N/App |
| Adapalene | >0.8 | >0.6* | >0.6* |
| 15-HETrE | >0.01, ≤0.05 | N/App | N/App |

*Precipitate observed in plates of 0.8 mg/mL and higher. MIC not achieved.
**dGLA supplied by Sigma, cat# E4504
***dGLA supplied by Cayman, cat# 90230

TABLE 5

Combinations of Antibacterial Compositions with HETrE

| Nicotinamide [mg/mL] | Growth Index (+++, ++, +, −) | | | |
|---|---|---|---|---|
| | Plate 1 | Plate 2 | Plate 3 | Avg |
| Nicotinamide + 0.01 mg/mL 15-HETrE (<MIC): | | | | |
| 1 | +++ | +++ | +++ | +++ |
| 5 | +++ | +++ | +++ | +++ |
| 10 | ++ | ++ | ++ | ++ |
| 15 | − | − | − | − |
| 25 | − | − | − | − |
| Nicotinamide + 0.05 mg/mL 15-HETrE (>MIC) | | | | |
| 1 | − | − | − | − |
| 5 | − | − | − | − |
| 10 | − | − | − | − |
| 15 | − | − | − | − |
| 25 | − | − | − | − |

| BPO [mg/mL] | Growth Index (+++, ++, +, −) | | | |
|---|---|---|---|---|
| | Plate 1 | Plate 2 | Plate 3 | Avg |
| Benzoyl Peroxide + 0.01 mg/mL 15-HETrE (<MIC): | | | | |
| 0.2 | +++ | +++ | +++ | +++ |
| 0.4 | +++ | +++ | +++ | +++ |
| 0.6 | ++ | ++ | ++ | ++ |
| 0.8 | + | + | + | + |
| 1.0 | − | − | − | − |
| Benzoyl Peroxide + 0.05 mg/mL 15-HETrE (>MIC) | | | | |
| 0.2 | − | − | − | − |
| 0.4 | − | − | − | − |
| 0.6 | − | − | − | − |
| 0.8 | − | − | − | − |
| 1.0 | − | − | − | − |

| Adapalene [mg/mL] | Growth Index (+++, ++, +, −) | | | |
|---|---|---|---|---|
| | Plate 1 | Plate 2 | Plate 3 | Avg |
| Adapalene + 0.01 mg/mL 15-HETrE (<MIC): | | | | |
| 0.2 | +++ | +++ | +++ | +++ |
| 0.4 | +++ | +++ | +++ | +++ |
| 0.6 | ++ | ++ | ++ | ++ |
| 0.7 | + | + | + | + |
| Adapalene + 0.05 mg/mL 15-HETrE (>MIC) | | | | |
| 0.2 | − | − | − | − |
| 0.4 | − | − | − | − |
| 0.6 | − | − | − | − |
| 0.7 | − | − | − | − |

| Metronidazole [mg/mL] | Growth Index (+++, ++, +, −) | | | |
|---|---|---|---|---|
| | Plate 1 | Plate 2 | Plate 3 | Avg |
| Metronidazole + 0.01 mg/mL 15-HETrE (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | +++ | +++ | +++ |
| Metronidazole + 0.05 mg/mL 15-HETrE (>MIC) | | | | |
| 0.2 | − | − | − | − |
| 0.4 | − | − | − | − |
| 0.6 | − | − | − | − |
| 0.8 | − | − | − | − |

15-HETrE in combination with other compounds including nicotinamide, metranidazole or benzoyl peroxide did not reduce the growth of P. Acnes below that of 15-HETrE used alone. However, a spike of 0.01 mg/ml HETrE to adapalene did reduce the MIC of adapalene from >0.8 to >0.6, ≤0.7. These results suggest that 15-HETrE and adapalene may exhibit synergy since 0.01 mg/ml HETrE has no effect on its own but when it is added to adapalene it is able to further decrease the growth rate of P. acnes below that of the 15-HETrE single compound treatment (see, Table 6).

TABLE 6

15-HETrE Combination Summary

| Compound | MIC (mg/mL) as per P-11-0007 or P-11-0008 Addendum A | MIC (mg/mL) with 0.01 mg/mL 15-HETrE spike | MIC (mg/mL) with 0.05 mg/mL 15-HETrE spike* |
|---|---|---|---|
| Metronidazole | >1 | >1 | <0.2 |
| Nicotinamide | >10, ≤15 | >10, ≤15 | <1 |
| BPO | >0.6, ≤0.8 | >0.6, ≤0.8 | <0.2 |
| Adapalene | >0.8 | >0.6, ≤0.7 | <0.2 |
| 15-HETrE | >0.01, ≤0.05 | N/App | N/App |

*0.05 mg/mL 15-HETrE is an inhibitory concentration so complete inhibition was expected for all plates spiked with 0.05 mg/mL.

TABLE 7

Combinations of Antibacterial Compositions with 15-OHEPA

| Nicotinamide [mg/mL] | Growth Index (+++, ++, +, −) | | | |
|---|---|---|---|---|
| | Plate 1 | Plate 2 | Plate 3 | Avg |
| Nicotinamide + 0.05 mg/mL 15-OHEPA (<MIC): | | | | |
| 1 | +++ | +++ | +++ | +++ |
| 5 | +++ | +++ | +++ | +++ |
| 10 | +++ | +++ | +++ | +++ |
| 15 | − | − | − | − |
| Nicotinamide + 0.1 mg/mL 15-OHEPA (>MIC) | | | | |
| 1 | − | − | − | − |
| 5 | − | − | − | − |
| 10 | − | − | − | − |
| 15 | − | − | − | − |

| BPO [mg/mL] | Growth Index (+++, ++, +, −) | | | |
|---|---|---|---|---|
| | Plate 1 | Plate 2 | Plate 3 | Avg |
| Benzoyl Peroxide + 0.05 mg/mL 15-OHEPA (<MIC): | | | | |
| 0.2 | +++ | +++ | +++ | +++ |
| 0.4 | ++ | ++ | ++ | ++ |
| 0.6 | + | + | + | + |
| 0.8 | − | − | − | − |
| 1.0 | − | − | − | − |
| Benzoyl Peroxide + 0.1 mg/mL 15-OHEPA (>MIC) | | | | |
| 0.2 | − | − | − | − |
| 0.4 | − | − | − | − |
| 0.6 | − | − | − | − |
| 0.8 | − | − | − | − |

| Adapalene [mg/mL] | Growth Index (+++, ++, +, −) | | | |
|---|---|---|---|---|
| | Plate 1 | Plate 2 | Plate 3 | Avg |
| Adapalene + 0.05 mg/mL 15-OHEPA (<MIC): | | | | |
| 0.2 | +++ | +++ | +++ | +++ |
| 0.4 | +++ | +++ | +++ | +++ |
| 0.6 | ++ | +++ | +++ | +++ |
| 0.7 | ++ | ++ | ++ | ++ |
| Adapalene + 0.1 mg/mL 15-OHEPA (>MIC) | | | | |
| 0.2 | − | − | − | − |
| 0.4 | − | − | − | − |
| 0.6 | − | − | − | − |
| 0.7 | − | − | − | − |

TABLE 7-continued

Combinations of Antibacterial Compositions with 15-OHEPA

| Metronidazole [mg/mL] | Growth Index (+++, ++, +, −) | | | |
|---|---|---|---|---|
| | Plate 1 | Plate 2 | Plate 3 | Avg |
| Metronidazole + 0.05 mg/mL 15-OHEPA (<MIC): | | | | |
| 0.2 | +++ | +++ | +++ | +++ |
| 0.4 | +++ | +++ | +++ | +++ |
| 0.6 | +++ | +++ | +++ | +++ |
| 0.8 | +++ | +++ | ++ | +++ |
| 1.0 | +++ | ++ | +++ | +++ |
| Metronidazole + 0.1 mg/mL 15-OHEPA (>MIC): | | | | |
| 0.2 | − | − | − | − |
| 0.4 | − | − | − | − |
| 0.6 | − | − | − | − |
| 0.8 | − | − | − | − |
| 1.0 | − | − | − | − |

15-OHEPA in combination with other compounds including nicotinamide, metranidazole or adapalene did not reduce the growth of P. Acnes below that of 15 OHEPA used alone. However, a spike of 0.05 mg/ml 15-OHEPA to benzoyl peroxide did reduce the MIC of benzoyl peroxide from >0.6, ≤0.8 to >0.4, ≤0.6. These results suggest that 15-OHEPA and benzoyl peroxide may exhibit synergy since 0.05 mg/mL has no effect on its own but when added to benzoyl peroxide it is able to further decrease the growth rate of P. acnes below that of the 15-OHEPA single compound treatment (see, Table 8).

TABLE 8

15-OHEPA Combination Summary

| Compound | MIC (mg/mL) as per P-11-0007 or P-11-0008 Addendum A | MIC (mg/mL) with 0.05 mg/mL 15-OHEPA spike | MIC (mg/mL) with 0.1 mg/mL 15-OHEPA spike* |
|---|---|---|---|
| Metronidazole | >1 | >1 | <0.2 |
| Nicotinamide | >10, ≤15 | >10, ≤15 | <1 |
| BPO | >0.6, ≤0.8 | >0.4, ≤0.6 | <0.2 |
| Adapalene | >0.8 | >0.8 | <0.2 |
| 15-OHEPA | >0.05, ≤0.075 | N/App | N/App |

*0.1 mg/mL 15-OHEPA is an inhibitory concentration. Complete inhibition was expected for all plates spiked with 0.1 mg/mL.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

What is claimed is:

1. A method for treating acne in a subject in need thereof, the method comprising: administering to the subject a pharmaceutical composition comprising a therapeutically effective amount of 15-hydroxy-eicosapentaenoic acid ("15-HEPE") or 15-hydroxy-eicosatrienoic acid ("15-HETrE").

2. The method of claim 1, wherein the pharmaceutical composition comprises about 0.1 wt. % to about 20 wt. % of 15-HEPE or 15-HETrE.

3. A method of treating acne in a subject in need thereof, the method comprising: topically administering to the subject a pharmaceutical composition comprising a therapeutically effective amount of dihomo-gamma-linolenic acid ("DGLA"), 15-HEPE, or 15-HETrE, wherein the pharmaceutical composition further comprises about 1.65 wt. % steareth-2, about 1.35 wt. % steareth-21, about 0.5 wt. % cetyl alcohol, about 0.2 wt. % ascorbyl palmitate, about 0.15 wt. % a-tocopherol, about 2.0 wt. % medium-chain triglycerides, about 2.0 wt. % myristyl myristate, about 4.0 wt. % isopropryl palmitate, about 1.0 wt. % glycerin, about 1.0 wt. % phenoxyethanol, about 0.1 wt. % ascorbic acid, about 0.8 wt. % carbomer, about 0.4 wt. % xanthan gum, about 0.5 wt. % liquid soy lecithin, and about 0.05 wt. % Mild Care 345 fragrance.

4. The method of claim 2, wherein the pharmaceutical composition comprising 15-HEPE further includes a therapeutically effective amount of benzoyl peroxide.

5. The method of claim 4, wherein the pharmaceutical composition comprises about 1.25% to about 10 wt. % of benzoyl peroxide.

6. The method of claim 2, wherein the pharmaceutical composition comprising 15-HETrE further includes a therapeutically effective amount of adapalene.

7. The method of claim 6, wherein the pharmaceutical composition comprises about 0.05 wt. % to about 0.3 wt. % of adapalene.

8. The method of claim 3, wherein the step of administering comprises topically applying the composition to an area of the skin afflicted with acne lesions.

9. The method of claim 8, wherein the area of the skin afflicted with acne lesions is first washed prior to application of the pharmaceutical composition.

10. The method of claim 8, wherein the acne lesions are inflammatory type and/or non-inflammatory type lesions.

11. The method of claim 10, wherein applying the composition results in about a 10%, 20%, 30%, 40%, 50% 50%, 70%, 80%, 90% or more reduction in number of acne lesions.

12. The method of claim 3, wherein the acne is associated with *Propionibacterium acnes*.

13. The method of claim 3, wherein the pharmaceutical composition is administered to the subject once a day, twice a day, or three times a day.

14. The method of claim 3, wherein the pharmaceutical composition is a cream.

15. The method of claim 3, wherein the subject previously exhibited acne lesions.

16. A method of treating acne vulgaris or acne necrotica in a subject in need thereof, the method comprising: topically administering to the subject a pharmaceutical composition comprising a therapeutically effective amount of DGLA, wherein the pharmaceutical composition further comprises about 1.65 wt. % steareth-2, about 1.35 wt. % steareth-21, about 0.5 wt. % cetyl alcohol, about 0.2 wt. % ascorbyl palmitate, about 0.15 wt. % a-tocopherol, about 2.0 wt. % medium-chain triglycerides, about 2.0 wt. % myristyl myristate, about 4.0 wt. % isopropryl palmitate, about 1.0 wt. % glycerin, about 1.0 wt. % phenoxyethanol, about 0.1 wt. % ascorbic acid, about 0.8 wt. % carbomer, about 0.4 wt. % xanthan gum, about 0.5 wt. % liquid soy lecithin, and about 0.05 wt. % Mild Care 345 fragrance.

17. The method of claim 16, wherein the pharmaceutical composition comprising DGLA further includes a therapeutically effective amount of benzoyl peroxide.

18. The method of claim 17, wherein the pharmaceutical composition comprises about 1.25% to about 10 wt. % of benzoyl peroxide.

19. The method of claim 16, wherein the step of administering comprises topically applying the composition to an area of the skin afflicted with acne lesions.

20. The method of claim 19, wherein the area of the skin afflicted with acne lesions is first washed prior to application of the pharmaceutical composition.

21. The method of claim 19, wherein the acne lesions are inflammatory type and/or non-inflammatory type lesions.

22. The method of claim 21, wherein the composition reduces about 10%, 20%, 30%, 40%, 50% 50%, 70%, 80%, 90% or more of the acne lesions.

23. The method of claim 16, wherein the acne is associated with *Propionibacterium acnes*.

24. The method of claim 16, wherein the pharmaceutical composition is administered to the subject once a day, twice a day, or three times a day.

25. The method of claim 16, wherein the pharmaceutical composition is a cream.

26. The method of claim 16, wherein the subject previously exhibited acne lesions.

27. A method for improving antimicrobial activity of an agent used in the treatment of acne, the method comprising: adding a composition comprising one or more of 15-HEPE or 15-HETrE to the agent.

28. The method of claim 27, wherein the composition comprises about 0.1 wt. % to about 20 wt. % of 15-HEPE or 15-HETrE.

29. A method for improving antimicrobial activity of an agent in the treatment of acne, the method comprising: adding a topically deliverable composition comprising one or more of DGLA, 15-HEPE, or 15-HETrE, wherein the composition further comprises about 1.65 wt. % steareth-2, about 1.35 wt. % steareth-21, about 0.5 wt. % cetyl alcohol, about 0.2 wt. % ascorbyl palmitate, about 0.15 wt. % a-tocopherol, about 2.0 wt. % medium-chain triglycerides, about 2.0 wt. % myristyl myristate, about 4.0 wt. % isopropryl palmitate, about 1.0 wt. % glycerin, about 1.0 wt. % phenoxyethanol, about 0.1 wt. % ascorbic acid, about 0.8 wt. % carbomer, about 0.4 wt. % xanthan gum, about 0.5 wt. % liquid soy lecithin, and about 0.05 wt. % Mild Care 345 fragrance.

30. The method of claim 29, wherein the composition comprising DGLA further includes a therapeutically effective amount of benzoyl peroxide.

31. The method of claim 30, wherein the composition comprises about 1.25 wt. % to about 10 wt. % of benzoyl peroxide.

32. The method of claim 28, wherein the composition comprising 15-HEPE further includes a therapeutically effective amount of benzoyl peroxide.

33. The method of claim 32, wherein the composition comprises about 1.25% to about 10 wt. % of benzoyl peroxide.

34. The method of claim 28, wherein the composition comprising 15-HETrE further includes a therapeutically effective amount of adapalene.

35. The method of claim 34, wherein the composition comprises about 0.05 wt. % to about 0.3 wt. % of adapalene.

36. A method of inhibiting *Propionibacterium acnes*, the method comprising: contacting *Propionibacterium acnes* with a pharmaceutical composition comprising 15-HEPE or 15-HETrE.

37. The method of claim 36, wherein the pharmaceutical composition comprises about 0.1 wt. % to about 20 wt. % of 15-HEPE or 15-HETrE.

38. A method of inhibiting *Propionibacterium acnes*, the method comprising: contacting *Propionibacterium acnes* with a pharmaceutical composition comprising DGLA, 15-HEPE, or 15-HETrE, wherein the pharmaceutical composition further comprises about 1.65 wt. % steareth-2, about 1.35 wt. % steareth-21, about 0.5 wt. % cetyl alcohol, about 0.2 wt. % ascorbyl palmitate, about 0.15 wt. % a-tocopherol, about 2.0 wt. % medium-chain triglycerides, about 2.0 wt. % myristyl myristate, about 4.0 wt. % isopropryl palmitate, about 1.0 wt. % glycerin, about 1.0 wt. % phenoxyethanol, about 0.1 wt. % ascorbic acid, about 0.8 wt. % carbomer, about 0.4 wt. % xanthan gum, about 0.5 wt. % liquid soy lecithin, and about 0.05 wt. % Mild Care 345 fragrance.

39. The method of claim 38, wherein the pharmaceutical composition comprising DGLA further includes a therapeutically effective amount of benzoyl peroxide.

40. The method of claim 39, wherein the pharmaceutical composition comprises about 1.25% to about 10 wt. % of benzoyl peroxide.

41. The method of claim 37, wherein the pharmaceutical composition comprising 15-HEPE further includes a therapeutically effective amount of benzoyl peroxide.

42. The method of claim 41, wherein the pharmaceutical composition comprises about 1.25% to about 10 wt. % of benzoyl peroxide.

43. The method of claim 37, wherein the pharmaceutical composition comprising 15-HETrE further includes a therapeutically effective amount of adapalene.

44. The method of claim 43, wherein the pharmaceutical composition comprises about 0.05% to about 0.3 wt. % of adapalene.

* * * * *